United States Patent [19]

Vander-Mallie

[11] Patent Number: 4,536,479
[45] Date of Patent: Aug. 20, 1985

[54] USE OF ANTI-IDIOTYPE ANTIBODIES IN IMMUNOASSAYS

[75] Inventor: Ronald Vander-Mallie, Nashua, N.H.

[73] Assignee: E. I. Du Pont de Nemours and Company, Wilmington, Del.

[21] Appl. No.: 477,611

[22] Filed: Mar. 22, 1983

[51] Int. Cl.$^3$ .................... G01N 33/54; G01N 33/52
[52] U.S. Cl. .................... 436/537; 436/800; 436/819; 435/4; 435/7; 435/25; 435/28
[58] Field of Search ............ 436/512, 518, 528–534, 436/536–541, 542–548, 800, 804, 805, 819, 822, 823, 824; 435/4, 7, 28, 14, 25

[56] References Cited

U.S. PATENT DOCUMENTS 4,048,298  9/1977  Niswender .................... 436/500

OTHER PUBLICATIONS

Reth, M. et al., *Eur. J. Immunology*, vol. 9, pp. 1004–1013, (12–1979).
Rauch, J. et al., *J. Immunology*, vol. 129(1), pp. 236–241, (7–1982).
Legrain, P. et al., *Eur. J. Immunology*, vol. 11, pp. 678–685, (1981).
Nelles, M. J., *J. Exper. Medicine*, vol. 154, pp. 1756–1763, (12–1981).
Potocnjak, P. et al., *Science*, vol. 215, pp. 1637–1639, (03-26-1982).
Eilat, D. et al., *Proc. Nat'l. Acad. Sci. USA*, vol. 79, pp. 3818–3822, (06–1982).
Buttin, G. et al., "Lymphocyte Hybridomas," *Current Topics in Microbiology & Immunology*, vol. 81, pp. 27–36, (1978).
Brient, B. W. et al., *J. Exper. Medicine*, vol. 132(5), pp. 951–962, (1970).
Kobzik, L. et al., Proc. Nat'l. Acad. Sci. USA, vol. 73(5), pp. 1702–1706, (5–1976).
Claflin, J. L., Journal of Immunology, vol. 112(5), pp. 1747–1756, (5–1974).
Bluestone, J. A. et al., Molecular Immunology, vol. 19(4), pp. 515–524, (4–1982).

*Primary Examiner*—Ben R. Padgett
*Assistant Examiner*—M. Moskowitz

[57] ABSTRACT

The use of anti-idiotype antibodies as functional substitutes for antigens or haptens in immunoassays is disclosed.

4 Claims, No Drawings

USE OF ANTI-IDIOTYPE ANTIBODIES IN IMMUNOASSAYS

TECHNICAL FIELD

This invention relates to immunoassays useful in the detection of clinically significant analytes in biological or other liquid test samples. In particular, this invention relates to the use of anti-idiotype antibodies as functional substitutes for antigenic or haptenic ligands in immunoassays of the prior art.

BACKGROUND ART

Immunoglobulins are high molecular weight proteins with the capacity to bind specific ligands. Although immunoglobulins are generally thought of as binding agents, they are also capable of being bound, i.e., one immunoglobulin may function as a ligand for another immunoglobulin which functions as a binding agent.

Immunoglobulins from a first species can serve as antigens when injected into a second species. The antiserum raised in the second species contains immunoglobulins directed against antigenic sites or determinants on the immunoglobulins from the first species. The antiserum and immunoglobulins contained therein are said to be heterologous with respect to the first species. Immunoglobulins from the same species are said to be homologous, while immunoglobulins from the same individual are said to be isologous.

The immunoglobulins from any given species can be divided into three broad categories based upon antigenic heterogeneity. Isotypes are those immunoglobulins which share a common effector function, e.g., immunoglobulin G is responsible for humoral immune response, while immunoglobulin E is responsible for the allergic response. The antigenic heterogeneity resides in the type of heavy chain out of which the immunoglobulin is formed. In the examples given, immunoglobulin G comprises a $\gamma$ chain, while immunoglobulin E comprises an $\epsilon$ chain.

Although all isotypes share a common function, small differences have been observed within a given isotype of different members of the same species. These differences, which are genetic in origin, account for the second category of immunoglobulins, allotypes.

The final category of immunoglobulin is the idiotype. Because an immunoglobulin of a given isotype and allotype is capable of binding any one of countless ligands with remarkable specificity, it is clear that the ligand binding region of an immunoglobulin directed against one ligand must be different from the ligand binding region of an immunoglobulin directed against another ligand. The difference is reflected in the amino acid sequence of the ligand binding region. Idiotypes are antibodies which are distinguishable on the basis of the chemical nature of at least their ligand binding regions and, therefore, on the basis of the chemical nature of the ligands which they are capable of binding. Idiotypes were first discovered by Oudin who injected anti-Salmonella antibody from a donor rabbit into an allotype-matched, non-immune recipient rabbit. Some recipient rabbits produced antibody directed against the anti-Salmonella antibody. [Oudin, J. and Michel, M., J. Exp. Med., Volume 130, 595, 619 (1969)].

Other researchers found that the idiotypic region comprises the ligand binding site, but that the two are not necessarily coterminus. See, for example, Brient et al., P.N.A.S. Volume 68, 3136 (1971) and Sher et al., J. Immunol., Volume 109, 176 (1972). This conclusion is based on the fact that a reaction of idiotype and anti-idiotype antibodies is, in many cases, only partially inhibitable by the ligand for which the idiotype is specific. As used herein, the term "idiotype" refers to the specific region of an immunoglobulin which imparts its idiotypic character.

With the advent of the radioimmunoassay (RIA) [Yalow and Berson, J. Clin. Invest., Volume 39, 1157 (1960)], the immunoassay became recognized as an exquisitely sensitive tool in the measurement of clinically important substances found at low concentrations in various body fluids.

U.S. Pat. No. 3,654,090 issued to Schuurs on April 4, 1972 teaches the use of an enzyme-substrate system to replace the radioactive label used in the RIA.

Both of these assays make use of a competitive reaction between a limited number of antibody molecules and both a labeled antigen and unlabeled antigen (either known amounts used to construct a standard curve or unknown amounts contained in test samples). The more unlabeled antigen in the reaction mixture, the less labeled antigen will be bound to the limited number of antibody molecules. One must be equipped with a method to detect the ratio of bound to free labeled antigen.

The earliest methods used a physical separation of antibody-bound labeled antigen from free labeled antigen. This type of assay, in which a separation step is employed, is referred to as a heterogeneous assay.

Another method to detect the extent of binding of labeled antigen makes use of a preexisting signal produced by the binding of antibody and labeled antigen which is then modulated, either raised or lowered, by the binding of the unlabeled antigen. Such methods are referred to as homogeneous. U.S. Pat. No. 4,233,402, issued Nov. 11, 1980 to Maggio et al. and U.S. Pat. No. 3,996,345, issued Dec. 7, 1976 to Ullman et al. are illustrative of such methods which may include enzyme-channeling and fluorescence quenching.

The assays referred to above all make use of antigen or hapten (a low molecular weight substance which is not immunogenic but is capable of being bound by specific anti-hapten antibodies) which is identical or immunochemically analogous to the analyte (the unknown being tested for). The antigen or hapten is labeled with reagent means for determining the extent to which the labeled antigen or hapten is bound to the antibody. The use of such substances presents problems in the various assay systems already developed in the art. For example, many antigens, especially bacterial and viral antigens, are difficult to isolate in pure form. Isolation of such antigens can pose significant health hazards. Some antigens or haptens may lack suitable functional groups for the attachment of label. Furthermore, it is often difficult to label an antigen or hapten without altering its structure to the point where it no longer competes for anti-analyte antibody as well as unlabeled antigen; this is especially true for haptens. Labeling an antigen or hapten may also cause instability and susceptibility to rapid degradation. Finally, immobilization of an antigen or hapten on a solid support may decrease its ability to bind to antibody. Consequently, there is a need for a ligand which can act as a functional substitute for antigen or hapten and which (1) can be safely isolated in large quantities without the need for laborious purification steps;

(2) offers multiple possible sites for the attachment of label;

(3) can be labeled without substantially diminishing its ability to compete for antibody;

(4) can be labeled without substantially diminishing its stability; and (5) can be bound to a solid support without substantial loss of immunoreactivity.

Although anti-idiotype antibodies have been known in the art for over a decade, their practical utility as ligands in clinical immunoassays has gone unrecognized. It is precisely the use of such anti-idiotype antibodies, primarily as labeled ligands, particularly in homogeneous assays, which forms the basis of the current invention.

DISCLOSURE OF THE INVENTION

The present invention resides in the use of anti-idiotype antibodies as functional substitutes for antigens or haptens in immunoassays which include the step of incubating an idiotypic, anti-analyte antibody, an antigen or a hapten, and an unknown amount of analyte, where at least one member of the group consisting of idiotypic, anti-analyte antibody, antigen and hapten is labeled with reagent means for determining the extent to which the antigen or hapten is bound to the idiotypic, anti-analyte antibody.

In particular, in a heterogeneous assay either the anti-idiotype antibody or the idiotypic, anti-analyte antibody is labeled. In a homogeneous assay, either or both antibodies are labeled.

DETAILED DESCRIPTION OF THE INVENTION

The present invention is applicable to immunoassays of the prior art in which an anti-analyte antibody is incubated with a labeled antigen or hapten, and a sample containing an unknown amount of analyte. (Analyte is chemically identical or immunochemically analogous to antigen or hapten.) One aspect of the present invention resides in the discovery that a labeled anti-idiotype antibody (antibody directed against the idiotypic region of the anti-analyte antibody) can substitute for the labeled antigen of the prior art and, at the same time, overcome the disadvantages and problems associated with the use of labeled antigen or labeled hapten. The labeled anti-idiotype antibody can be used in heterogeneous as well as homogeneous assays.

Anti-idiotype antibody can be made by injecting anti-analyte antibody into an animal thereby eliciting antiserum against various antigenic determinants on the anti-analyte antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) must usually be coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material. Anti-analyte antibodies can be produced either by conventional immunization or by somatic cell fusion (hybridoma) techniques, in which case the anti-analyte antibodies will be polyclonal or monoclonal, respectively.

Polyclonal anti-idiotype antibodies can be prepared by immunizing an animal with an immunoglobulin fraction of the anti-analyte antibody prepared as described above. In general, it is desirable to immunize an animal which is species and allotype-matched with the animal in which the anti-analyte antibody was raised. This minimizes the production of antibodies directed against non-idiotypic determinants. The antiserum so obtained is then usually absorbed extensively against normal serum from the same species in which the anti-analyte antiserum was raised, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Not all anti-idiotype antibodies are analyte-inhibitable. Since only those antibodies which are analyte-inhibitable are useful in the immunoassays of this invention, it is sometimes necessary to further purify the anti-idiotype antiserum by contacting it with a solid phase having coated thereon idiotypic anti-analyte antibodies, followed by analyte elution. Only those antibodies which are analyte-inhibitable will elute from the solid phase.

Monoclonal anti-idiotype antibodies can be produced using the method of Kohler and Milstein, Nature, Volume 256, 495 (1975). This production requires an anti-analyte antibody as an immunogen. The anti-analyte antibody can be either monoclonal or polyclonal, the former being preferred. If polyclonal, it is prepared as described above.

If the anti-analyte antibody is to be monoclonal, it can be prepared using hybridoma technology which comprises fusing (1)spleen cells from a mouse immunized with the antigen or hapten-carrier conjugate of interest to (2) a mouse myeloma cell line which has been selected for resistance to a drug (e.g., 8-azaguanine). In general, it is desirable to use a myeloma cell line which does not secrete an immunoglobulin. Several such lines are known in the art. A preferred cell line is P3X63Ag8.653. This cell line is on deposit at the American Type Culture Collection as CRL-1580.

Fusion can be carried out in the presence of polyethylene glycol according to established methods. [See, for example, Monoclonal Antibodies, R. Kennett, J. McKearn & K. Bechtol, eds. N.Y., Plenum Press, 1980 and Current Topics in Microbiology & Immunology, Volume 81, F. Melchers, M. Potter & N. L. Warner, eds., N.Y., Springer-Verlag, 1978.]The resultant mixture of fused and unfused cells is plated out in hypoxanthine-aminopterin-thymidine (HAT) selective medium. Under these conditions, only hybrid cells will grow.

When sufficient cell growth has occurred, (typically 10–14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures which remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

Monoclonal anti-idiotype antibodies are prepared by repeating the procedure described above, using the monoclonal (or polyclonal) idiotypic, anti-analyte antibody as the immunogen. In general, it is preferable to use the same inbred strain of mouse for making the anti-idiotype antibody as was used for making the idiotypic, anti-analyte antibody, as this reduces the number of antibodies to unwanted antigenic determinants (e.g., allotypic determinants). However, different inbred strains can be used, and, in fact, even different species can be used.

Screening the hybrid clones for monoclonal anti-idiotype antibody is performed as described earlier for monoclonal, idiotypic, anti-analyte antibodies.

Anti-idiotype antibodies, like anti-analyte antibodies, can be directly labeled by various methods known in the art. Label serves as reagent means for determining the extent to which the anti-idiotype antibody is bound by idiotypic, anti-analyte antibody in an immunoassay. Label can be a radioisotope, enzyme, chromophore, fluorophore, light-absorbing or refracting particle, etc. It is preferable to label the antibody as extensively as possible without destroying its immunoreactivity. As described earlier, anti-idiotype antibodies provide convenient functional groups for attachment of label. The epsilon-amino groups of lysine are useful for labeling as are the sugar groups in the Fc region of the molecule. Free sulfhydryl or S-sulfonate groups on Fab' fragments and half-molecules, respectively, are also useful. Known hetero and homobifunctional reagents can be used to attach label to the antibody. Iodine-125 can be incorporated into tyrosine residues by using, for example, Chloramine T [Greenwood, Hunter, and Glover, J. Biochem., Volume 89, 144 (1963)] or lactoperoxidase [Marchalonis, Biochem. J., Volume 113, 229 (1969)]. Following labeling, it may be desirable to purify the antibodies by immunoaffinity chromatography to ensure that the final product is immunoreactive.

Particularly in heterogeneous assays, it is also possible to indirectly label the anti-idiotype antibody with a labeled antibody directed against a non-idiotypic, antigenic determinant on the anti-idiotype antibody, e.g., a directly labeled, heterologous antibody directed against a determinant in the Fc region of the anti-idiotype antibody.

Anti-idiotype antibodies can be used as either divalent or monovalent antibodies. Monovalent antibodies such as Fab and Fab' can be produced by well known methods.

One aspect of the present invention is the use of labeled anti-idiotype antibodies produced by any of the foregoing methods as substitutes for labeled antigens and labeled haptens in heterogeneous and homogeneous immunoassay methods of the prior art.

The labeled anti-idiotype antibody can be used as a substitute for the labeled antigen in the radioimmunoassay method first described by Berson and Yalow in 1960 as well as in the numerous variations described subsequent thereto.

The labeled anti-idiotype antibody can also be used as a substitute for the labeled antigen in the heterogeneous, enzyme-linked immunosorbent assay first described in U.S. Pat. No. 3,654,090 issued to Schuurs on Apr. 4, 1972 and incorporated herein by reference, as well as in the numerous variations described subsequently thereto.

The labeled anti-idiotype antibody can also be used as a substitute for the labeled antigen (or ligand) in the homogeneous fluorescence quenching assay described in U.S. Pat. No. 3,996,345, issued Dec. 7, 1976, and in the homogeneous enzyme channeling assay described in U.S. Pat. No. 4,233,402, issued Nov. 11, 1980, both of which are incorporated herein by reference. Example 3, below, demonstrates the use of a labeled anti-idiotype antibody in a homogeneous enzyme channeling assay. Example 4, below, demonstrates the use of a labeled anti-idiotype antibody in a homogeneous fluorescence quenching assay.

Another aspect of this invention is the use of a nonlabeled anti-idiotype antibody in a heterogeneous immunoassay in which the antibody, rather than the antigen is labeled. A typical assay of this type makes use of a solid phase such as the wall of a test tube or microtiter plate or particle having coated thereon an antigen which is identical or immunochemically analogous to the analyte of interest. An aliquot of test sample and an aliquot of labeled anti-analyte antibody are contacted with the solid phase. The more analyte in the test sample, the more labeled anti-analyte antibody will bind to it leaving a proportionally smaller amount to bind to the solid phase. A nonlabeled anti-idiotype antibody as described herein can be used as a substitute for the nonlabeled antigen in such immunoassay systems.

The following examples illustrate the use of anti-idiotype antibodies as functional substitutes for antigens or haptens in known immunoassay methods.

EXAMPLE 1

Heterogeneous Assay

The following example illustrates the use of a nonlabeled anti-idiotype antibody as a ligand in a heterogeneous assay for human IgE.

The following abbreviations apply:
E: human IgE
MaE: monoclonal mouse anti human IgE (Id)
RaMaE: rabbit anti-(monoclonal mouse anti human IgE) (aId)

In the context of this invention, MaE is the idiotypic, anti-analyte antibody and RaMaE is the anti-idiotype antibody.

Monoclonal mouse anti-human IgE (MaE) was produced using the method described by Kohler and Milstein (1975). An IgE myeloma protein was used for immunization and another IgE myeloma protein was used for screening. The cell line P3X63Ag8 UI (a non-secretor cell line) was used for fusion.

The MaE was isolated from the ascites of Balb/c mice in which the hybridoma was being passed. The ascites was fractionated using 50% saturated ammonium sulfate, and the MaE was obtained by affinity chromatography on IgE-Sepharose-4B (antibody was dissociated from the solid phase using 3 M ammonium thiocyanate, pH 7.4).

Polyclonal RaMaE was prepared by immunizing white New Zealand rabbits with MaE. For immunization, 1.2 mL of affinity purified monoclonal anti-IgE in borate buffered saline (BBS), pH 8.4, at a concentration of approximately 1 mg/mL was mixed with 0.4 mL of Protein A-Sepharose-4B (Sigma). This solution was incubated for at least one hour at room temperature and then the solution was mixed with an equal volume of either complete (primary injection) or incomplete Freund's adjuvant (booster injections). The resulting 3.2 mL solution was injected in equal volumes into three white New Zealand rabbits. The rabbits were injected five times: days 0, 15, 27, 35, and 49. Bleeds were taken every week after the fourth injection.

Immune serum harvested after the fourth week was purified by absorbing it with normal mouse serum coupled to Sepharose-4B and then further purifying it using Sepharose-Protein A chromatography. A final purification to make the antibody anti-idiotype specific was performed by absorbing the antiserum with normal mouse ascites coupled to Sepharose 4B.

The purified RaMaE was diluted in BBS, pH 8.3, to a final concentration of about 10 µg/ml. The wells of a microtiter plate were coated with RaMaE by applying 100 µL of RaMaE and incubating for 6 hours at room temperature. Control wells were prepared by adding 100 µL of BBS. After the incubation, all wells were washed three times with a 0.05% solution of Triton X-100 in phosphate buffered saline (PBS), pH 7.4. To prevent non-specific adsorption, the wells were coated again with bovine serum albumin (BSA) by adding 300 µL of a solution of BSA (1%), normal mouse serum (2%) and merthiolate (0.01%) in BBS. The contents of the wells were incubated overnight at 4° C. The wells were then washed three times with a 0.05% solution of Triton X-100 in PBS.

An $^{125}I$ labeled MaE was prepared using the method of Greenwood & Hunter. The iodinated MaE (approx. 15 µCi/µg) was then diluted in a solution of 1% BSA in BBS with 0.01% merthiolate to give a solution with about $10^5$ counts per minute (CPM) per 100 µL determined using a gamma scintillation counter with 70% efficiency.

Human myeloma IgE was then added to the $^{125}I$-MaE prepared above to give final IgE concentrations of 0, 1, 2, 5, 10, 25 and 50 µg/µL. The $^{125}I$-MaE and IgE were allowed to pre-incubate for 24 hours at 4° C.

One hundred microliters of each IgE - $^{125}I$-MaE solution was applied to the RaMaE coated and control microtiter plate wells as described above. The contents of the wells were incubated for six hours at 37° C. The contents of each well were aspirated. The wells were then washed three times with a 0.05% solution of Triton X-100 in PBS, separated from the microtiter plate, and counted individually for one minute in glass test tubes. The data were as follows:

| µg/ml IgE | CPM (average of duplicates) | % Bound* |
|---|---|---|
| 0 | 1518 | 100.0 |
| 1 | 1297 | 85.4 |
| 2 | 1230 | 81.1 |
| 5 | 1191 | 78.5 |
| 10 | 1098 | 72.4 |
| 25 | 1115 | 73.5 |
| 50 | 935 | 61.6 |
| Control | 173 | 0 |

$$\% \text{ Bound} = \frac{\text{CPM-background}}{\text{O-background}} \times 100$$

where background is the CPM of the control wells (173 CPM)

The data show that a dose response curve was obtained, and as little as 1 µg/ml of IgE was detectable.

The radioisotope label can be replaced with an enzyme, chromophore, fluorophore, light refractive particle, etc. Alternatively, the extent to which Id and aId are bound can be determined by use of indirect labeling, e.g., a directly labeled third antibody directed against an antigenic determinant in the Fc region of the anti-analyte antibody.

EXAMPLE 2

Homogeneous Enzyme Channeling Assay

The following example illustrates the use of a labeled anti-idiotype antibody as a labeled ligand in a homogeneous assay for NIP-CAP which is defined below.

The following abbreviations apply:
NP: 3-nitro-4-hydroxy-phenylacetic acid
NIP: 3-nitro-4-hydroxy-5-iodophenylacetic acid
NIP-CAP: amide formed from NIP and 6-aminocaproic acid
NP-BSA: NP coupled to bovine serum albumin
Id: Monoclonal anti-NP antibody having an idiotypic determinant recognized by anti-idiotype antibody. The former antibody can bind NP or the structurally similar NIP group.
aId: Anti-idiotype antibody directed against the idiotypic region of Id.
HRP: Horseradish peroxidase
GO: Glucose oxidase
PBS: Phosphate buffered saline Monoclonal antibody directed against the hapten NP (Id) and monoclonal anti-idiotype antibody directed against Id (aId) were obtained using the general methods of Kohler and Milstein (1975). The preparation of these antibodies has been described in the following publications: Reth, M., Hammerling, G. J., and Rajewsky, K., Eur. J. Immunol., Volume 8, 393-400 (1978) and Reth, M., Imanishi-Kari, T., and K. Rajewsky, Eur. J. Immunol., Volume 9, 1004-1013 (1979). Both Id and aId antibodies were IgG molecules and were prepared using cell lines P8.86.9 and AC 146, respectively.

The anti-NP antibody (Id) has an idiotypic region which functionally overlaps the antigen binding site. Thus the binding of the hapten NP (or the structurally similar group NIP with which the antibody cross-reacts) inhibits the binding of Id to aId.

Id was purified from the ascites of Balb/c mice in which the hybridoma was grown. After fractionation using 50% ammonium sulfate, the immunoglobulin fraction was affinity purified on NP-BSA-Sepharose-4B. Id was eluted from the column using 0.1 M acetate buffer, pH 4.8. After dialysis and concentration, Id was labeled with GO using a modification of the 2 step glutaraldehyde procedure described by Avrameas and Ternyek, Immunochem., Volume 8, 1175 (1971).

Anti-Id, semipurified by ammonium sulfate precipitation, was conjugated with HRP using a modification of the periodate procedure described by Wilson and Nakane, Immunofluorescence and Related Techniques, Knopp, et al., Elsevier, Holland, 215 (1978).

Three immunoassays were performed. In the first assay, Id-GO and aId-HRP were both used at $1 \times 10^{-8}$M concentration in the final reaction mixture (dilutions in PBS, pH 7.4, with 0.1% gelatin). NIP-CAP was tested at 0, 1, 2, 5, and 20µg/mL final concentration in the reaction mixture. The second assay was identical to the first except that Id-GO and aId-HRP were used at $5 \times 10^{-8}$M concentration in the final reaction mixture. The third assay was identical to the first two except that Id-GO and aId-HRP were used at $2.5 \times 10^{-7}$M concentration in the final reaction mixture.

The following were added to 13 × 100 mm glass test tubes:

| | |
|---|---|
| Id-GO | 0.25 ml |
| aId-HRP | 0.25 ml |
| NIP-CAP | 0.50 ml |

The resulting reaction mixture was incubated for 1 hour at room temperature, after which 2 mL of a substrate solution containing 0.60 mg/mL orthophenylene diamine; 22.6 mg/ml β-D-glucose and 60% glycerol in phosphate buffer pH 7.0 was added. The solutions were then incubated at room temperature until color developed. The reactions were stopped after identical periods of incubation by adding 1.0 mL of 4.5 N $H_2SO_4$. The absorbance at 492 nm ($A_{492}$) was read against a blank. The results are shown below

| NIP-CAP (µg/mL) | $A_{492}$ (Id-GO, aId-HRP at $1 \times 10^{-8}$M) | $A_{492}$ (Id-GO, aId-HRP at $5 \times 10^{-8}$M) | $A_{492}$ (Id-GO, aId-HRP at $2.5 \times 10^{-7}$M) |
|---|---|---|---|
| 0 | .221 | 1.001 | 1.391 |
| 1 | .175 | .909 | 1.296 |
| 2 | .203 | .896 | 1.304 |
| 5 | .209 | .795 | 1.114 |
| 20 | .172 | .709 | 1.058 |

The optimal sensitivity was obtained when Id-GO and aId-HRP were each used at a concentration of $5 \times 10^{-8}$M.

Other suitable enzyme channeling systems are described in U.S. Pat. No. 4,233,402.

EXAMPLE 3

Homogeneous Latex Particle Agglutination Assay

The following example illustrates the use of an anti-idiotype coated particle as a labeled ligand in a homogeneous assay for NIP-BSA which is defined below.

The following abbreviations apply:
NIP-BSA: NIP conjugated to BSA
BBS: Borate buffered saline, pH 8.3
Id: Same as Example #2, above
aId: Same as Example #2, above
NP: Same as Example #2, above Monoclonal antibody directed against NP and bearing an idiotypic region which functionally overlaps the antigen binding site was the same as that referred to in Example #2. The antigen-inhibitable monoclonal anti-idiotype antibody specific for anti-NP antibody was also the same as that described in Example #2. Both antibodies were purified in the same manner as described in Example #2.

The anti-idiotype antibody was adsorbed onto latex particles (Sigma 0.8 micron average particle diameter) by incubating latex (0.4% w/v) and anti-idiotype antibody (15 µg/mL) in 0.054 M glycine-saline buffer, pH 8.2, as described in Practical Immunology, Hudson & Hay, 2nd Edition, p. 137-138 (1980). Coated and washed latex particles were stored at a 0.4% w/v concentration in glycine-saline buffer containing BSA (1 mg/mL). The efficiency of coupling was approximately 48% as determined by protein recovery.

The approximate, minimal agglutinating concentration of anti-NP antibody was determined by a preliminary experiment, after which the following experiment was performed: One drop of BSA dissolved in diluent (BBS with 1 mg/mL gelatin, pH 8.3) or diluent containing varying concentrations of the antigen NIP-BSA was placed in the center of separate circles marked on the surface of three agglutination slides. To the antigen and BSA solutions was added two drops of 0.4% w/v latex particles coated with aId or normal mouse immunoglobulin (NMIg). Finally, one drop of Id (90 µg/mL) in diluent was added. The contents were mixed with a wood toothpick and then the slides were rocked in a circular motion. After incubating at 20°-22° C. for 15 minutes, the results were read by eye. Agglutination was visible as clumping of the latex particles. The results are shown below.

| NIP-BSA µg/mL | BSA µg/mL | LATEX | AGGLUTINATION SCORE |
|---|---|---|---|
| 1000 | | latex-anti-Id | − |
| 200 | | | − |
| 40 | | | − |
| 8 | | | + |
| 0.8 | | | ++ |
| 0 | | | +++ |
| 0 | 100 | | +++ |
| 0 | 0 | latex-NMIg | − | where
+++indicates very strong agglutination
++indicates mild agglutination
+indicates weak agglutination
−indicates no agglutination The presence of antigen correlated with inhibition of agglutination. Inhibition was specific for the antigen NIP-BSA. This example shows the ability of NIP-BSA to inhibit the reaction between Id and aId antibodies. In this example, a latex particle was used as the label. Other light absorbing or refracting particles can also be used as the label.

EXAMPLE 4

Homogeneous Fluorescence Quenching Assay

This example illustrates the use of a fluorescein-labeled idiotypic, anti-levan antibody and a rhodamine-labeled anti-idiotype antibody in a homogeneous fluorescence quenching immunoassay for the analyte levan. This assay is based on the principle that when two appropriate fluorophores interact via fluorescence energy transfer, the fluorescence of the donor fluorophore (e.g., fluorescein) will be quenched by energy transfer to an acceptor fluorophore (e.g., rhodamine). In this system, the interaction of the fluorophores is made possible by the binding of the fluorescein-labeled idiotypic, anti-levan antibody to the rhodamine-labeled anti-idiotype antibody. This binding can lead to the quenching of the fluorescein fluorescence whose magnitude is a direct indicator of the idiotype/anti-idiotype interaction. Upon addition of levan, the analyte in this example, the idiotype/anti-idiotype interaction is inhibited, resulting in the reduction of the quenching of the fluorescein fluorescence. This reduction is directly related to the amount of levan added.

Monoclonal mouse idiotypic, anti-levan antibody (Id) and monoclonal mouse anti-idiotype antibody were obtained as ascites fluids of Balb/c mice. The production of the hybridomas which were used in the preparation of these antibodies has been described. [Eur. J. Immunol., Volume 11, 678–685 (1981)]. Both antibodies were fractionated to obtain the IgG portion by DE-52 ion exchange chromatography. Affinity purified Id was isolated using a levan-Sepharose-6B affinity column. The antibody was eluted with 0.1 M glycine-HCl buffer, pH 2.8. Affinity purified aId was prepared using an Id-Sepharose-4B affinity column. Adsorbed antibody was eluted with 3 M ammonium thiocyanate, pH 7.5. Id was labeled with fluorescein by reacting fluorescein isothicyanate (FITC) with Id at pH 7.2 in phosphate buffer. The fluorophore to protein ratio was approximately 4. Anti-Id was labeled with rhodamine by reacting tetramethyl rhodamine isothiocyanate (TRITC) with the anti-idiotype antibody at pH 9 in borate buffer.

Fluorescence was measured using a fluorescence spectrometer. Excitation and emission slit widths were set at 10 nm. Into a cuvette, the following were added:

| | |
|---|---|
| PBS, pH 7.5 | 2.5 mL |
| FITC-Id (60 g/mL) | 0.25 mL |
| TRITC-aID (26 g/mL) | 0.20 mL |

Varying volumes of a 1 mg/mL solution of levan were then added. The sample was radiated with light at 495 nm. Relative fluorescence at 520 nm was measured and percentage quenching calculated. The results are shown below.

| Levan (mg) | Relative Fluorescence | % Quenching |
|---|---|---|
| 0 | 37.0 | 18.1 |
| 0.1 | 38.0 | 15.9 |
| 0.15 | 39.8 | 11.9 |
| 0.20 | 41.2 | 8.8 |
| 0.25 | 42.2 | 6.6 |
| 0.30 | 43.0 | 4.9 |
| 0.35 | 44.2 | 2.2 |

The results show that a dose-response curve was obtained and that as little as 0.1 mg of levan could be detected.

The homogeneous fluorescence immunoassay may be expanded to include other fluorescence energy transfer system pairs, where the emission spectrum of one fluorophore overlaps well with the excitation spectrum of the other. Other known fluorophore pairs that may be applied to a homogeneous fluorescence immunoassay of an analyte using the Id-aId system are fluorescein-eosin or fluorescamine-eosin. The spectral characteristics of these fluorophores are shown below.

| Fluorophore | Excitation $\lambda$ (nm) | Emission $\lambda$ (nm) |
|---|---|---|
| Tetramethyl rhodamine | 520 | 550 |
| Fluorescein | 495 | 520 |
| Eosin | 520 | 545 |
| Fluorescamine | 390 | 520 |

I claim:

1. A homogeneous immunoassay for the detection of a nonimmunoglobulin analyte in a test sample, comprising:
   (1) contacting the test sample with reagents comprising:
      (a) a first covalent conjugate comprising a first enzyme and an idiotypic anti-analyte antibody;
      (b) a second covalent conjugate comprising a second enzyme and an anti-idiotypic antibody capable of competing with the analyte for the idiotypic anti-analyte antibody;
      (c) a substrate for the first and or second enzyme wherein one of the enzymes and the substrate are capable of reacting to produce a first product, which product is a substrate for the other enzyme, which is capable of reacting with the first product to produce a second, detectable product; and
   (2) measuring the amount of second product which is inversely related to the amount of analyte initially present in the test sample.

2. The immunoassay of claim 1 wherein one enzyme is glucose oxidase, the substrate is glucose and the other enzyme is horseradish peroxidase.

3. A homogeneous immunoassay for the detection of a nonimmunoglobulin analyte in a test sample comprising:
   (1) forming a reaction mixture by contacting the test sample with reagents, comprising:
      (a) a first covalent conjugate comprising a first fluorophore and an idiotypic anti-analyte antibody; and
      (b) a second covalent conjugate comprising a second fluorophore and an anti-idiotypic antibody capable of competing with the analyte for the idiotypic anti-analyte antibody;
   wherein one of the fluorophores is capable of absorbing incident light at a wavelength $\lambda_{inc}$ to produce light emission at wavelength $\lambda_{em1}$ which can be absorbed by the other fluorophore to produce emission at wavelength $\lambda_{em2}$;
   (2) irradiating the reaction mixture with light of wavelength $\lambda_{inc}$; and
   (3) measuring the intensity of light of wavelength $\lambda_{em1}$ or $\lambda_{em2}$, which intensity is related to the amount of analyte initially present in the test sample.

4. The immunoassay of claim 3 wherein one fluorophore is rhodamine and the other fluorophore is fluorescein.

* * * * *